United States Patent [19]

Collins et al.

[11] Patent Number: 4,587,121

[45] Date of Patent: May 6, 1986

[54] HIGH TITER PSEUDOMONAS IMMUNE SERUM GLOBULIN

[75] Inventors: Michael S. Collins, Richmond; Robert E. Roby, Pinole, both of Calif.

[73] Assignee: Miles Laboratories, Inc., Elkhart, Ind.

[21] Appl. No.: 504,106

[22] Filed: Jun. 17, 1983

[51] Int. Cl.$^4$ .................. A61K 39/395; A61K 39/40; C07K 15/00; C07K 3/00

[52] U.S. Cl. ........................................ 424/87; 424/85; 424/101; 530/387; 530/831

[58] Field of Search .................... 424/85, 87, 92, 101; 260/112 R, 112 B

[56] References Cited

U.S. PATENT DOCUMENTS

| | | | |
|---|---|---|---|
| 2,793,203 | 5/1957 | Schultze et al. | 424/87 |
| 4,027,010 | 4/1975 | Kiselen et al. | 424/87 |
| 4,120,950 | 10/1978 | Homma | 424/87 |
| 4,285,936 | 8/1981 | Peer et al. | 424/88 |
| 4,482,483 | 11/1984 | Curry et al. | 424/87 |

OTHER PUBLICATIONS

Chemical Abstracts, vol. 86, Abstract No. 68043x, 1977.
Chemical Abstracts, vol. 99, Abstract No. 191214z, 1983.
Chemical Abstracts, vol. 77, Abstract No. 99601w, 1972.

*Primary Examiner*—Blondel Hazel
*Attorney, Agent, or Firm*—Lester E. Johnson

[57] ABSTRACT

Normal plasma from donors who have not been vaccinated with a Pseudomonas vaccine or had a Pseudomonas infection can be screened for higher than normal titers of naturally occurring antibody to four of seven Fisher Immunotypes for Pseudomonas. Those plasmas with higher titers of such antibody can be pooled and fractionated to give hyperimmune serum globulin having high titers of antibody against all seven Fisher Immunotypes. The product may be treated to render it intravenously injectable and the so-prepared material is effective in treating patients with Pseudomonas infection.

12 Claims, No Drawings

HIGH TITER PSEUDOMONAS IMMUNE SERUM GLOBULIN

BACKGROUND OF THE INVENTION

1. Field of the Invention:

This invention relates to and has among its objects novel immune serum globulins and novel methods for their production. Particularly, the invention is concerned with immune serum globulins having a high titer of naturally occurring antibody to lipopolysaccharide antigens of *Pseudomonas aeruginosa*. Further objects of the invention will be evident from the following description wherein parts and percentages are by weight unless otherwise specified.

2. Description of the Prior Art:

Hyperimmune serum globulins, i.e., immune serum globulin having high titers of a particular antibody, are therapeutically useful in treating patients with antibody immunodeficiency. For example, tetanus hyperimmune globulin is useful in treating tetanus and rabies hyperimmune globulin, rabies. It is well known that hyperimmune serum globulins can be produced from plasma or serum obtained from selected donors who have much higher titers for a specific antibody than is normally found in the average population. These donors have either been recently immunized with a particular vaccine (U.S. Pat. No. 4,174,388) or else they have recently recovered from an infection or disease [Stiehm, *Pediatrics*, Vol. 63, No. 1, 301–319 (1979)]. These high titer sera or plasmas are pooled and subjected to the usual Cohn fractionation procedures up to the point of isolating Fraction II [Cohn et al, *J. Am. Chem. Soc.*, 68, 459 (1946) and Oncley, et al, ibid, 71, 541 (1949)].

Although infection with *Pseudomonas aeruginosa* (*P. aeruginosa*) is not common among the general population, *P. aeruginosa* infection is encountered very frequently in certain susceptible groups of patients. Burn victims and immunosuppressed cancer patients have been identified as having an unusually high risk of acquiring severe, and sometimes fatal, *P. aeruginosa* infection. *P. aeruginosa* infections are usually acquired during a hospital stay, not at home.

*P. aeruginosa* is resistant to penicillin G. A combination of *P. aeruginosa* specific penicillin and an aminoglycoside is the usual therapy for *P. aeruginosa* sepsis and has greatly contributed to the survival of patients, particularly leukemics. The management of *P. aeruginosa* in burn patients is also dependent upon topical antimicrobial therapy.

James et al, in *The Lancet*, 13 Dec. 1980, 1263–1265, described passive immunization of burn patients at risk of septicaemia. The immunization was accomplished with an immunoglobulin prepared from plasma from healthy human volunteers vaccinated with a polyvalent Pseudomonas vaccine. There is, of course, some risk in vaccinating healthy volunteers in order to increase their titer of antibody in plasma.

Zaia et al in *The Journal of Infectious Diseases*, Vol. 137, No. 5, 601–604 (1978) disclosed a practical method for preparation of Varicella-Zoster (VZ) Immune Globulin. Outdated blood was screened for complement-fixing antibody to VZ virus. About 15% of the plasma units had a titer greater than or equal to 16, with about 7.5% greater than or equal to 32.

Fisher et al have identified seven non-cross-protective immunotypes of *P. aeruginosa* (Fisher et al, *Journal of Bacteriology*, May 1969, p. 835–836, which is incorporated herein by reference). The authors developed an antigen scheme for *P. aeruginosa* based on challenge protection in mice as distinguished from serological tests in vitro.

SUMMARY OF THE INVENTION

We have found that normal plasma from donors who have not been vaccinated with a Pseudomonas vaccine or had a recent Pseudomonas infection can be screened for higher than normal titers of antibody to four of the seven immunotypes (Fisher et al) in *P. aeruginosa*. Those plasmas with titers greater than about 1:1600 can be pooled and then fractionated to give a *P. aeruginosa* hyperimmune gamma globulin that has a high titer of antibody to lipopolysaccharide antigens of all seven Fisher immunotypes and can offer significant protection against all seven of the Fisher immunotypes. This result is quite surprising because it is unexpected that plasma from normal donors not vaccinated or not having had a recent Pseudomonas infection would have a titer of antibody to *P. aeruginosa* high enough to yield, when pooled and fractionated, a Pseudomonas hyperimmune globulin which shows significant effectiveness in treating *P. aeruginosa* infections. Furthermore, it is surprising that screening for only four of the seven Fisher immunotypes and pooling the plasma reflecting higher than normal titers for only four of the seven Fisher immunotypes would yield a hyperimmune serum globulin that provides significant protection against all seven of the Fisher immunotypes.

One obvious advantage of the invention is that normal donors need not be given a vaccine. Consequently, any risks inherent in such a practice are avoided. Another advantage of the invention is that the hyperimmune globulin obtained offers immediate protection and may be treated to render it intravenously injectable, thus avoiding patient discomfort associated with intramuscular administration. Furthermore, less product need be administered intravenously in order to achieve the same level of prevention or cure obtained with an intramuscularly administered product.

DESCRIPTION OF THE PREFERRED EMBODIMENTS

These and other advantages of the present invention may be obtained in the following manner.

Normal plasma from a donor is screened for naturally occurring antibody to lipopolysaccharide antigens of *P. aeruginosa* of Fisher immunotypes 1, 2, 4, and 6 employing an enzyme-linked immunosorbent assay (ELISA) or other equally sensitive screening method such as radioimmune assay, etc. To be significantly effective it has been found that the plasma from such donors should have a titer of antibody to the aforementioned Fisher immunotypes greater than about 1:1600. About 2–5% of plasma donors have such titers. A hyperimmune serum globulin obtained in this manner contains higher than normal titers of antibody to all seven Fisher immunotypes and can be significantly effective against all seven of the Fisher immunotypes for *P. aeruginosa*, thus, being effective in treating patients suffering from *P. aeruginosa* infection.

The method of screening the plasma, i.e., the ELISA method, is essentially as described by Engvall and Perlmann, *J. Immunol.*, 109, 129–135 (1972), Engvall et al, *Biochemica Et Biophysica Acta*, 251 (1971) 427–434, Engvall et al, *Immunochemistry*, 8, 871–874 (1971), Voller et al, *Bull. World Health Organ.*, 51, 209–211, (1974), and Voller et al, ibid., 53, 55–65 (1976) which are all incorporated herein by reference. The assay is a simple method for the quantitative determination of antibodies. Wells of polystrene 96 well microtiter plates coated with antigen are incubated with antiserum followed by an enzyme-labeled preparation of anti-immunoglobulin. The enzyme remaining in the tubes after washing provides a measure of the amount of specific antibodies in serum. Using the ELISA method 1–100 nanograms/ml of antibody can be determined.

Plasma having a sufficiently high titer of antibody to Fisher immunotypes 1, 2, 4, and 6 of *P. aeruginosa* is pooled and fractionated to obtain an immune serum globulin. To this end one may employ any method for obtaining an intravenously injectable immune serum globulin from pooled plasma. For example, one may employ the Cohn fractionation method (referenced hereinabove, which references are incorporated herein by reference thereto) to give Cohn Fraction II, ammonium sulphate fractionation, gel chromatography, semipermeable membrane filtration, or the like. The immune serum globulin of the invention has a titer of antibody to Fisher immunotypes 1, 2, 4, and 6 of at least 1:6400 and to Fisher immunotypes 3, 5, and 7 of at least 1:1600. The aforementioned immune serum globulin comprises IgG, usually at least 90% of IgG monomer. The material generally also contains other gamma globulins such as IgA, IgM, and the like.

As mentioned above, the *P. aeruginosa* hyperimmune globulin may be intramuscularly or intravenously injectable. The latter material is preferred and may be prepared, for example, according to the method of U.S. Pat. No. 3,903,262 (which is incorporated herein by reference) or any of the methods referred to in the above-identified U.S. patent. The modified immune serum globulin of U.S. Pat. No. 3,903,262 is adapted for intravenous injection and consists of intact immune serum globulin chains having partly intact interchain disulfide linkages. Each cleaved disulfide linkage is replaced by a pair of alkylated mercapto groups, the cleaved chains remaining united by non-covalent association so that the apparent molecular weight of the modified serum globulin in non-dissociating solvents is substantially the same as unmodified immune serum globulin. The above material is produced by selectively reducing a mildly alkaline aqueous solution of an immune serum globulin with dithiothreitol or dithiolrythritol, alkylating the thus-reduced interchain disulfide groups, and separating the thus-modified globulin from the non-proteinaceous reaction products.

The hyperimmune globulin preparation of this invention can also include maltose as a stabilizer in accordance with the teaching of U.S. Pat. No. 4,186,192. Accordingly, the instant preparation may contain about 1–20% of maltose on a weight to volume basis.

The hyperimmune products of the invention may be incorporated into pharmaceutical preparations, usually aqueous solutions of the hyperimmune serum globulin which may be used for therapeutic purposes. However, the term "pharmaceutical preparation" is intended in a broader sense herein to include preparations containing a hyperimmune serum globulin in accordance with this invention used not only for therapeutic purposes, but also for reagent purposes as known in the art; for tissue culture wherein organisms such as viruses for the production of vaccines and the like, are grown on plasma or on plasma fractions, e.g., Cohn Effluent II+III, Cohn Fraction IV, Cohn Fraction V, and so forth; etc.

The pharmaceutical preparation intended for therapeutic use should contain a therapeutic amount of hyperimmune serum globulin, i.e., that amount necessary for preventative or curative health measures. If the pharmaceutical preparation is to be employed as a reagent, then it should contain reagent amounts of hyperimmune serum globulin. Similarly, when used in tissue culture or a culture medium the preparation should contain an amount of hyperimmune serum globulin sufficient to obtain the desired growth.

EXAMPLES

The invention is demonstrated further by the following illustrative examples.

ASSAY METHOD

The assay method was essentially the same as that described by Voller et al, supra. Two hundred microliters (200 μl) of antigen (5 μg/ml) in carbonate buffer pH 9.6 was added to each well of polystyrene microtiter plates and incubated at 37° C. for 3 hours. The plates were washed once with phosphate buffered saline (PBS) containing 0.05% Tween 20 and allowed to drain. Serum was diluted in PBS-Tween. Fifty (50) μl of PBS-Tween 20 was added to each well. An initial dilution of serum (1:50) was made in a Wasserman tube. Serial two-fold dilutions were made from this dilution in a microtiter plate using a 50 μl microtiter loop. The first dilution in the plate was 1:100. After completion of the serial two-fold dilutions, the volume in the wells was made up to 200 μl with 150 μl of PBS Tween 20. The final dilution in each well was thus increased fourfold. The plates were incubated overnight at room temperature and then washed three times. Two hundred (200) μl of goat anti-human IgG conjugated to alkaline phosphotase diluted 1:1000 in PBS-Tween 20 was added to the wells and incubated at room temperature for 4 hours. After washing the plates four times with PBS Tween 20, 200 μl of enzyme substrate p-nitrophenylphosphate (Sigma Chemical Co., Saint Louis, Missouri) 1 mg/ml of diethanolamine buffer was added to each well and was allowed to incubate at room temperature for 30 minutes. The yellow color which developed was quantitated spectrophotometrically at 405 nm. A dilution of normal serum at 1:1,600 gave absorbence (OD) readings less than 0.05. Therefore, a serum diluted 1:1,600 having an OD reading of 0.1 or greater is considered positive.

The materials and reagents employed in the above procedure were:

PBS-Tween 20—with 0.05% Tween 20.

Carbonate buffer—0.06M; pH 9.5—1.91 g $Na_2CO_3$, 3.52 g $NaHCO_3$ in 1 liter of distilled water.

Diethanolamine buffer 10%; pH 9.8—pH adjusted with 1M HCL. (Note: 0.02% $NaN_3$ was added to the above reagents to prevent bacterial growth).

Goat anti-human IgG conjugated with alkaline phosphotase (Miles Laboratories, Elkhart, Indiana).

Polystyrene microtiter plates—Dynatech Laboratories Cat. # 1-220-24X.

12—channel pipette and multi-tips, Flow Laboratories Cat. # 77-889-00.

EXAMPLE 1

Plasma obtained from donors was screened for titer to antibody to Fisher immunotypes 1, 2, 4, and 6 *P.*

*aeruginosa* using the above-described ELISA method. Titer is that dilution giving an $OD_{405nm} \geq 0.1$.

Plasma with a *P. aeruginosa* Fisher immunotypes 1, 2, 4, and 6 titer of 1:1600 or greater were pooled. The pooled sera (0.1 ml) were used to passively immunize mice three hours before challenge with 20 $LD_{50}$ of *P. aeruginosa*. (20 $LD_{50}$ = 20×the dose needed to kill 50% of challenged mice).

As controls, pools of sera were prepared having a titer of antibody to *P. aeruginosa* of less than 1:400, 1:400, and 1:800. Mice were similarly injected with one of these pooled sera prior to challenge with 20 $Ld_{50}$ of *P. aeruginosa* as mentioned above.

The results are summarized in Table 1.

TABLE 1

| ELISA titer | Sera in Pool No. | % Total | Cumulative Mortality | $P^a$ |
|---|---|---|---|---|
| <1:400 (control) | 160 | 64.5 | 10/10 | |
| 1:400 (control) | 41 | 16.5 | 8/10 | $NS^b$ |
| 1:800 (control) | 24 | 9.7 | 8/10 | NS |
| 1:1600 | 23 | 9.3 | 4/10 | .05 |

$^a$Statistical significance.
$^b$NS is not significant protection by chi-square test.

EXAMPLE 2

Sixteen donors from Example 1 donated additional plasma 1-3 months after the donation of Example 1. The titer of antibody to *P. aeruginosa* by ELISA in eight sera samples was 1:1600 or greater; in the other eight samples the titer was 1:800 or greater.

The pooled sera were injected into mice as in Example 1 and the mice challenged with *P. aeruginosa* as above. Sera with a titer less than 1:400 and saline were the controls.

The results are summarized in Table 2.

TABLE 2

| ELISA titer | Sera in Pool No. | Cumulative Mortality | % Mortality | P |
|---|---|---|---|---|
| 1:400 (control) | 160 | 46/60 | 76.7 | NS |
| 1:800 | 8 | 88/160 | 55.0 | .004 |
| 1:1600 | 8 | 53/155 | 34.2 | .0001 |
| Saline (control) | — | 30/38 | 78.9 | |

EXAMPLE 3

The pooled sera with titer of antibody to Fisher immunotypes 1, 2, 4, and 6 to *P. aeruginosa* of 1:1600 or greater was fractionated to give an intravenous immune serum globulin (IGIV). The ammonium sulfate fractionation method of Heide et al, "Handbook of Experimental Immunology", 3rd edition, 1979I, was employed. 880 mg total protein was purified by chromatography on Sephadex G-200 530 ml column. As a control, normal sera was fractionated by the above method to produce an IGIV.

The antibody distributions of the hyperimmune IGIV of the invention and the control are summarized below in Table 3.

TABLE 3

| Fisher Immunotype | Antibody titer$^{-1}$ by ELISA | | Antibody Increase (× fold) |
|---|---|---|---|
| | Hyperimmune Pseudomonas$^a$ IGIV 5% | Normal IGIV 5% | |
| 1 | 6,400 | 800 | 8 |
| 2 | 6,400 | 1,600 | 4 |
| 3 | 3,200 | 800 | 4 |
| 4 | 12,800 | 800 | 16 |
| 5 | 3,200 | 800 | 4 |
| 6 | 6,400 | 800 | 8 |
| 7 | 6,400 | 1,600 | 4 |

$^a$Prepared from equal volumes of plasma screened for IgG to immunotypes 1, 2, 4, and 6.

EXAMPLE 4

The so-fractionated hyperimmune Pseudomonas IGIV of Example 3 as well as sera from Example 3 were administered to mice as described in Example 1 and the mice challenged as in Example 1.

The results are summarized in Table 4.

TABLE 4

| ELISA titer | Cumulative mortality after 3 days |
|---|---|
| IgG (1:6400) | 2/10 |
| Sera (1:1600) | 4/10 |
| Sera (1:400) | 9/10 |

What is claimed is:

1. A method for preparing an immune serum globulin having a high titer of antibody to lipopolysaccharide antigens of *P. aeruginosa* of Fisher immunotypes 1-7 which comprises:
   (a) screening plasma from donors who have not been vaccinated with a Pseudomonas vaccine or had a recent Pseudomonas infection for a titer of unattenuated antibody to lipopolysaccharide of *P. aeruginosa* of Fisher immunotypes 1, 2, 4, and 6 which is 1:1600 or greater,
   (b) pooling plasma of said titer of antibody, and
   (c) preparing an immune serum globulin from said pooled plasma.

2. The method of claim 1 which further includes the step of rendering the immune serum globulin of step c intravenously injectable.

3. The method of claim 1 wherein donor plasma is screened by an enzyme-linked immunosorbent assay.

4. The method of claim 1 wherein the immune serum globulin is produced by the Cohn fractionation method.

5. The method of claim 1 wherein the immune serum globulin is produced by an ammonium sulfate fractionation method.

6. The method of claim 1 wherein the immune serum globulin is reduced and alkylated to render it intravenously injectable.

7. The method of claim 1 wherein the immune serum globulin comprises IgG.

8. An immune serum globulin having a titer of antibody to lipopolysaccharide antigens of *P. aeruginosa* of Fisher immunotypes 1, 2, 4, and 6 of at least 1:6400 produced by the method of claim 1.

9. The immune serum globulin of claim 8 having a titer of antibody to lipopolysaccharide antigens of *P. aeruginosa* of Fisher immunotypes 1-7 sufficient to render the immune serum globulin effective in treating *P. aeruginosa* infections.

10. A pharmaceutical preparation comprising an aqueous solution of the immune serum globulin of claim 8.

11. The preparation of claim 10 which further includes maltose.

12. The immune serum globulin of claim 8 which is intravenously injectable.

* * * * *

UNITED STATES PATENT AND TRADEMARK OFFICE
CERTIFICATE OF CORRECTION

PATENT NO. : 4,587,121
DATED : May 6, 1986
INVENTOR(S) : Michael S. Collins, Robert E. Roby It is certified that error appears in the above-identified patent and that said Letters Patent are hereby corrected as shown below:

On the information-bearing front page in the above-identified patent, the filing date should be 06/14/83

Signed and Sealed this

Fifth Day of August 1986

[SEAL]

Attest:

Attesting Officer

DONALD J. QUIGG

Commissioner of Patents and Trademarks